United States Patent [19]
Sanz et al.

[11] Patent Number: 4,569,357
[45] Date of Patent: Feb. 11, 1986

[54] METHOD FOR CARDIOGONIOMETRY

[75] Inventors: Ernst Sanz, Zaeziwil; Jean-Pierre Steger, Ittigen; Werner Thie, Wabern, all of Switzerland

[73] Assignee: Ernst Sanz, Switzerland

[21] Appl. No.: 464,765

[22] Filed: Feb. 7, 1983

[30] Foreign Application Priority Data

Feb. 12, 1982 [CH] Switzerland ............... 898/82

[51] Int. Cl.⁴ .............................................. A61B 5/04
[52] U.S. Cl. ..................................................... 128/699
[58] Field of Search ............... 128/644, 695, 696, 699, 128/702, 703, 709, 710

[56] References Cited

U.S. PATENT DOCUMENTS

| | | | |
|---|---|---|---|
| 3,186,403 | 6/1965 | Bassett | 128/709 |
| 3,534,727 | 10/1970 | Roman | 128/644 |
| 3,822,696 | 7/1974 | Ekstrom et al. | 128/703 |
| 3,884,221 | 5/1975 | Eastman | 128/699 |
| 3,991,747 | 11/1976 | Stanly et al. | 128/709 |
| 4,106,495 | 8/1978 | Kennedy | 128/699 |

FOREIGN PATENT DOCUMENTS

| | | | |
|---|---|---|---|
| 1237702 | 6/1960 | France | 128/644 |
| 274612 | 7/1951 | Switzerland | 128/644 |

Primary Examiner—William E. Kamm
Attorney, Agent, or Firm—Roylance, Abrams, Berdo & Goodman

[57] ABSTRACT

A cardiogoniometry or vector cardiography system wherein signals directly derived from the bioelectrical field are not directly processed as orthogonal data but are instead especially orthogonalized in an analog computing network. Orthogonalization is based on a derivation electrode configuration space with sloping sagittal and frontal planes. The orthogonalized signals are processed in a cardiogoniometer and are also jointly recorded on a commercial electrocardiograph in parallel thereto. All the represented data which can be used for diagnosis purposes are referenced to a biological zero line, which differs from the electrical neutral point. The cardiogoniometer permits a vectorial real time measurement on the patient.

16 Claims, 13 Drawing Figures

|   | PHI | αR | βR | TR | αT | βT | TT | INT |
|---|---|---|---|---|---|---|---|---|
| 1 | 15 | 104 | 12 | 41 | 120 | 14 | 321 | 770 |
| 2 | 12 | 104 | 9 | 42 | 116 | 15 | 322 | 821 |
| 3 | 14 | 103 | 8 | 41 | 117 | 13 | 334 | 824 |
| 4 | 8 | 103 | 10 | 39 | 112 | 13 | 306 | 832 |
| 5 | 9 | 105 | 9 | 46 | 113 | 13 | 336 | 867 |
| 6 | 10 | 105 | 10 | 44 | 115 | 13 | 338 | 854 |
| 7 | 10 | 104 | 11 | 47 | 115 | 14 | 329 | 845 |
| 8 | 7 | 106 | 10 | 46 | 113 | 14 | 335 | 876 |
| 9 | 10 | 102 | 7 | 41 | 112 | 12 | 341 | 898 |
| 10 | 8 | 106 | 9 | 42 | 114 | 10 | 331 | 841 |
| MEAN | 10.3 | 104.2 | 9.5 | 42.9 | 114.7 | 13.1 | 329.3 | 842.8 |
| DEV | 2.5 | 1.25 | 1.36 | 2.5 | 2.37 | 1.3 | 9.9 | 33.3 |

METHOD FOR CARDIOGONIOMETRY

This invention relates to the field of cardiography, particularly vector cardiography, and more specifically relates to a cardiogoniometry process involving the spatial vector representation of electrical quantities of the heart, and a cardiogoniometer for processing these electrical quantities and for representing the parameters derived therefrom for the diagnosis of heart diseases.

BACKGROUND OF THE INVENTION

The evaluation of an electrocardiogram includes the determination of the maximum vector in the electrical QRS quantity in the frontal plane and is described by such terms as "left position", "steep position", etc. In addition, the direction of the repolarization vector, i.e., the behavior of the electrically detectable T-wave, is considered, particularly with respect to the direction of the QRS-vector (concordant or discordant behavior of the T-wave). An example is the behavior of the R and T components in the course of a myocardial infarction and the recovery therefrom. However, these evaluations are only possible in a roughly qualitative manner and, in addition, they are often considerably falsified by projection-caused errors because they are based only on the projection of these vectors on a plane but fail to take account of the divergence of the vectors or of components thereof perpendicular to the plane.

The following conclusions can be drawn on the basis of the ambiguity of the projections known from the representing geometry. All ECG derivations are projections of the true angle in space onto a plane. It is standard practice to consider a concordant T as normal and a discordant T as abnormal. Both can be correct, but as a result of the ambiguity of the projections, both can also be incorrect. Experience has shown that it is very difficult to evaluate a T-wave as to whether it is normal or pathological.

Thus, it is not possible to make a conclusive evaluation without knowing the behavior of the two associated vectors in space. It is therefore necessary to use a three-dimensional or orthogonal derivation system to obtain more accurate information and for quantitatively determining changes to the maximum vectors of QRS and T.

The presently recognized method for the construction of orthogonal derivations (Paul Lichtlen, *Klinische Vektor-Elektrokardiographie*, published by Springer, Berlin, Heidelberg, New York) consists of measuring individual local electrical voltages on the surface of a thorax model, the voltages being produced by an internally introduced artificial electric dipole. Accompanied by the upstream connection of a resistance network, these voltages are combined to form three derivations which correspond to the projection of the artificial electric dipole on the frontal, sagittal and horizontal planes of the thorax model. This takes place under the idealized assumption that the electrical field is, as a simplification, a dipole with a fixed neutral point.

This constitutes the SVEC III system of Schmitt and Simonson (1955), that of Frank (1956), and that of McFee and Parungao (1961). The reproducibility in all of the systems is good and they are recognized as being equivalent to each other. However, even the authors have admitted that all three systems give precise orthogonal derivations of only a model and the orthogonality can not be strictly obtained on humans due to individual variations in body dimensions and individual heterogeneous electrical conductivity characteristics in the tissues surrounding the heart. It is therefore not surprising that measurements on the same test subject with each of the three systems can easily lead to diverging results, with regard to vector direction (azimuth and elevation) as well as to the vector length i.e., the magnitude (Schmitt 1956, Tuna 1980).

A further disadvantage of these three systems is the complicated derivation technology with 14, 7 or 9 electrodes. As a result, the method is complicated for clinical use and is also very fault-prone so that it has not, as yet, become widely used in a routine manner in clinics.

The search for a simpler derivation system has revealed that it should be theoretically possible to construct orthogonal derivations from only four points on the thorax. This idea is not new and, in 1936, Schellong developed a derivation system with four electrodes. Using the term "vector diagram", the employed three derivations at right angles to one another, namely a horizontal from two points, the infraclavicular left (point zero) and right (point one), a vertical from point zero downwards to the thorax, approximately to point V of Wilson (referred to by Schellong as point three) and a sagittal from point zero to the dorsal (point two). He considered these three derivations as projections of the dipole and, in each case, linked two of these to form a loop which he made visible with a Braun tube. However, this technically simple method proved to be inaccurate and there were distortions of the loop. Duchosal and Sulzer (1949) used the same cubic system but, to avoid these distortions, chose the zero point (the origin of the system of coordinates of three axes) as far away as possible from the heart, namely in the back of the body to the rear and to the right. However, this system was also not adopted, although the coincidence with the biophysical derivation system SVEC III of Frank and McFee was not all bad (cf. Schmitt, 1956). The lack of precision of all cubic systems is due, *inter alia*, to the premise that each bipolar derivation represents the direct projection of the dipole moment of the heart. This can not be so, because each derivation is merely a potential difference measurement, i.e., a non-directional or scalar quantity, whereas the dipole moment, apart from its magnitude, also has a clearly defined direction, i.e., a vector character (Irnich, 1976).

BRIEF DESCRIPTION OF THE INVENTION

An object of the present invention is to provide a simple and reliable method for obtaining orthogonal projections of vector quantities.

A further object is to provide a process permitting, on the basis of the derivations in accordance with the invention, a determination of the true angle in space between the maximum vectors of the QRS-loop and the T-loop. The locations of the two maximum vectors of QRS and T is to be made possible by their projections on two planes.

A further object of the invention is to provide an apparatus for performing the method.

Briefly described, the invention includes a method for detecting electrical, heart-related signals in the natural bioelectric field of a human body comprising the steps of providing four electrodes electrically connected to an apparatus for recording and analyzing electrical signals produced at the electrodes, positioning a first one of the electrodes at point V4 according to Wilson, positioning a second one of the electrodes at point V8 according to Wilson, positioning a third one of the electrodes substantially vertically upwardly with respect to the upright body, above the first electrode at a distance equal to the distance between the first and second electrodes multiplied by a factor having a value between 0.6 and 0.8, and positioning the fourth one of the electrodes along a line substantially perpendicular to the line between the first and third electrodes and toward the right body side therefrom at a distance equal to the distance between the first and second electrodes multiplied by a factor having a value between about 0.6 and 0.8. In another aspect, the invention includes an apparatus for processing electrical signals representative of cardiac activity, the signals being of the type derived from the human body, the signals being referenced to a coordinate system, comprising coordinate transformation means for transforming the signals from one coordinate system to another, means for sampling the coordinate—transformed signals, means for digitizing the sampled signals, and means for evaluating the digitized signals.

BRIEF DESCRIPTION OF THE DRAWINGS

In order that the manner in which the foregoing and other objects are attained in accordance with the invention can be understood in detail, particularly advantageous embodiments thereof will be described with reference to the accompanying drawings, which form a part of this specification, and wherein:

FIG. 6' is a diagram showing the fixing of the range of T and R in polar coordinates;

THEORETICAL DISCUSSION OF THE INVENTION

Before going into a detailed description of the invention itself, certain important points will be briefly reviewed. The path to the development of a new model representative of the dipole moment is opened by temporarily ignoring the individual derivations, i.e., the individual electrical signals derived from the human body by the placement of electrodes thereon, and considering, as a whole, the electrical conditions in a plane formed by three derivation points. When using, in the electrocardiogram, the concept of a closed mesh, e.g., in the form of Nehb derivations D, A and I, (W. Nehb, Das Brustwarzen-Elektrokardiogramm, "Verhandlung der Deutschen Gesellschaft fur Kreislaufforschung" vol. 12, p. 177 (1939)) when considering the electrical conditions in a triangle formed by appropriate placement of electrodes (FIG. 1) a relative measure for the size of the dipole moment can be approximately obtained from the magnitude of the deflections of the electrocardiograph. Naturally, large or small simultaneous deflections will always give the sum zero, corresponding to the rules of Kirchoff's Law. However, when considering the potential differences given by these three derivations as partial vectors, and when they are summed according to the rules of vectorial addition, taking into account the size of the deflections and their polarity on the one hand and the derivation direction on the other, a sum vector is obtained which, in the presently represented model, can be looked upon as a dipole moment of the heart in its entirety. Thus, $$\vec{V} = \vec{D} + \vec{A} + \vec{I}.$$

On the basis of this, it is possible to obtain three orthogonal projections x, y and z from four near-heart derivation points and without the upstream connection of the previously required resistance network. Derivations D, A and I are differences of electrical potential as measured between two electrodes such as E2 and E4, E1 and E4, and E1 and E2, as shown in FIG. 1.

Naturally, it is not possible to claim absolute accuracy for this new vector construction model. This is due to the heterogeneous conductivity characteristics of the tissues surrounding the heart, which varies from individual to individual, but which is of a constant magnitude for an individual patient so that there is no need to correct it in the way which is required in previous empirical or cubic systems (Schellong, Duchosal, etc.). Due to the heterogeneity of the electrical field and, consequently the lack of knowledge of the electric flux line gradient at the derivation points according to the invention, neither the magnitude nor the direction determination of the dipole is completely accurate, but constancy and long-term reproducibility is obtained for the individual patient, as established by hundreds of measurements. This result is greatly assisted by the simple and reliable derivation method in accordance with the invention.

DETAILED DESCRIPTION OF THE PREFERRED EMBODIMENTS

Figure 1:
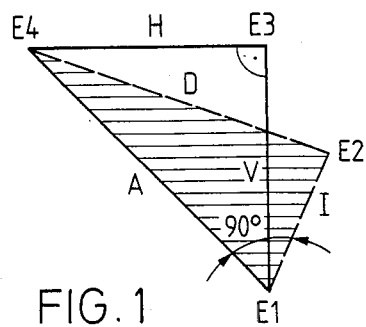
FIG. 1 is a diagram illustrating the four point electrode placement and derivation system in accordance with the invention.

FIG. 1 shows the four-point derivation system in accordance with the invention. The tetrahedral derivation system, which is to be considered in a spatial sense, shows the four electrode attachment points E1, E2, E3 and E4. These derivation points are connected in the following way: electrodes E1 and E2 are connected as a lower pair I, the location of electrode E1 corresponding to point V4 according to Wilson and is, indeed, 5ICR (intercostal space) and MCL (medioclavicular line); and point E2 which is sagittal to E1, and which corresponds to point V8 according to Wilson. Derivation point E3 is perpendicularly above point E1 and with a preferred spacing of $1/\sqrt{2}$ times the distance from E1 to E2, this dimension being vertical and designated V. The horizontal dimension H defined by points E3 and E4 is arranged horizontally and extends toward the right hand side of the patient also for a distance $1/\sqrt{2}$ times the distance between E1 and E2. Reference is also made to the dorsal derivation D defined by points E2, E4, and the anterior derivation A (E1, E4), the spacing between which is determined by the previously described relationships. An additional perpendicular from point E3 to the anterior derivation is designated $z_o$. In this representation, the plane containing A and I represents the sloping sagittal x,y plane, Z and A represents the frontal y,z plane, and Z,I the z, x-plane. The pair of derivation points E2, E3 is an unused plane and, as a redundant pair, is not taken into consideration. This does not mean, however, that diagnostically relevant information cannot be gathered from this derivation.

The two derivation points E2, E3 are relatively uncritical with respect to their positions relative to the patient's heart; in other words, manipulation deviations within certain limits during the fitting of these electrodes always lead to the same result. The derivation point with electrode E3 is located on relatively displaceable tissue perpendicularly above the heart apex electrode E1, whose position must be very accurately determined. This derivation point E3 is displaced relative to the geometry employed and, consequently, the heart, particularly during position changes of the patient during the measurement. However, this does not lead to erroneous measurements. The electrode 3 has limited sensitivity to displacement of the tissue or to location errors which can be looked upon as an advantage of the measurement technique. The measurement is not significantly influenced by position changes of the patient. It is pointed out that distinctions are always made between x, y, z-projections and the corresponding electrical derivations or their signals.

The electrodes are fitted to the patients in the following way for the derivation:

1. E1 corresponding to point V4 (Wilson) equals 5 ICR and MCL;
2. E2 sagittal to E1 (corresponding to point V8, Wilson);
3. E3 perpendicularly above E1 at the distance 0.7 times the distance between E1 and E2;
4. E4 horizontal to the right side of the patient at a distance of 0.7 times the distance between E1 and E3; and
5. The ground electrode is preferrably fitted to the patient's right arm.

This is a preferred procedure for fitting the electrodes to the patient. However, it is pointed out that for heart diagnosis on animals, only the geometrical electrode configuration appropriate for the particular animal should be used for derivation, while for determining the orthogonal derivation it is merely necessary to provide the coordinate transformation stage with adequate parameters. Thus, the invention is equally suitable for use in the heart diagnosis of animals and of humans.

When considering subjects with a healthy heart, the vector loop passes from the upper front right to the bottom front left and, after reversal, back again to the upper front right, i.e., the vector loop is to a greater or lesser extent in or parallel to a plane sloping with respect to the sagittal (according to FIG. 1, the area between the three derivation points E1, E2 and E4). ECG derivations in this plane must consequently react in a very sensitive manner to changes of the vector loop and this has been confirmed on well over 2,000 ECG measurements. This plane is used for constructing two perpendicularly directed projections, x and y and the frontal plane is used for constructing a projection $z_o$ perpendicular to the Nehb plane.

In order to obtain a right triangle as the derivation triangle, which is advantageous for trigonometric reasons, unlike in the case of Nehb, point V7 is not chosen as the dorsal derivation point of the triangle inclined with respect to the sagittal. Instead, V8 corresponding to E2 is chosen which is sagittal to point V4, corresponding to E1 (apex of heart). Thus, a right angle is obtained over the apex: derivation A is perpendicular to derivation I according to conventional ECG terminology. In addition, derivation point V8 corresponding to E2 can be clearly determined and easily found. By choosing point V8 according to Wilson as a dorsal derivation point, we obtain with points E1, E2, E4 a plane which is hereinafter called the sloping sagittal plane. The derivation designations D, A and I used by Nehb are maintained.

Figure 2:
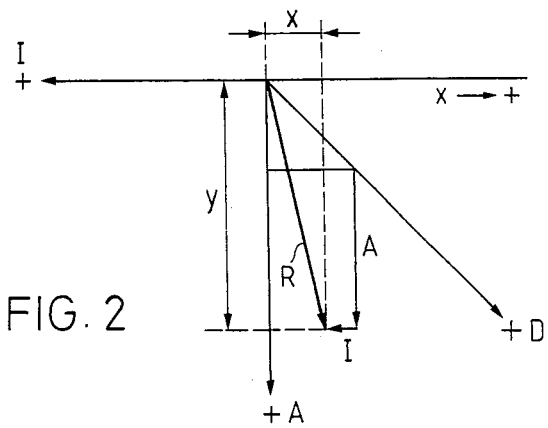
FIG. 2 is a diagram illustrating a projection and the formation of a sum vector therefrom.

When choosing the y axis of the present orthogonal system parallel to derivation A and the x axis parallel to derivation I, derivation A can not be assumed to be a projection of the vector on axis y and derivation I cannot be considered as a projection of the vector on axis x. In fact, for vector construction purposes, all three derivations D, A and I must be vectorially added in the form $\vec{V} = \vec{D} + \vec{A} + \vec{I}$. The thus formed summation vector is projected onto the x and y axes, as shown in FIG. 2. The following formulas are obtained after trigonometric calculations:

$$X = D \cos 45° - I = 0.7D - I \quad (1)$$

$$Y = D \sin 45° + A = 0.7D + A \quad (2)$$

Figure 3:
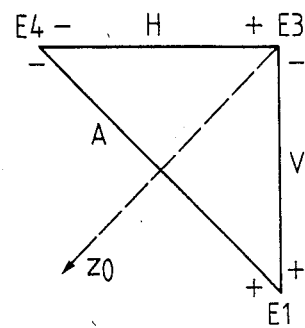
FIG. 3 is a diagram showing the formation of the frontal plane with three derivations.

An additional vector projection, which is perpendicular to these two axes, is required as the third axis in the orthogonal system. This projection $z_o$ is obtained by derivation in the frontal triangle of points E1, E3 and E4, points E1 and E4 representing the frontal derivation points of the sloping sagittal triangle. Point E3 is chosen in such a way that it is equidistant from points E1 and E4 and a right angle exists between these two lines as shown in FIG. 3. In this way, a right isosceles triangle is obtained. The following derivations apply in this triangle: horizontal derivation H from E4 to E3, vertical derivation V from E3 to E1, and anterior derivation A from E1 to E4, this being identical to derivation A in the sloping sagittal triangle D, A, I. Using the same procedure, it is also possible to construct a vector in this frontal triangle by interlinking the simultaneous deflections of the three derivations in correct sign and axis manner for vector summation. The interest of this sum vector is its projection on the axis $z_o$ in FIG. 3. This $z_o$ axis is perpendicular to A from point E3 and, consequently, is perpendicular to the sloping sagittal plane. As this perpendicular represents the angle bisector of the right angle point E3, this projection $z_o$ of the vector can be trigonometrically represented as $(V-H) \sin 45°$. When this expression has a positive sign, this vector is below the sloping sagittal plane, whereas with a negative sign it is above the sloping sagittal plane. In other words, the $z_o$ axis is positive when directed downwardly and negative when directed upwardly and is always perpendicular to the sloping sagittal plane, i.e., perpendicular to axes x and y. In summary, it can be stated the three orthogonal projections x, y and z are:

$$x = D \cos 45° - I = 0.7D - I \quad (1)$$

$$y = D \sin 45° + A = 0.7D + A \quad (2)$$

$$z = (V-H) \sin 45° = 0.7 (V-H) \quad (3)$$

The calculation of the maximum vectors of QRS, P and T and the determination of the solid angle $\phi$ between two of these maximum vectors is performed in accordance with the conventional space-trigonometric procedure. The space vectors are designated 1 and 2 and their projections on the x, y and z axes are designated $x_1$, $y_1$, $z_1$ or $x_2$, $y_2$, $z_2$, these quantities belonging to an orthogonal, spatial coordinate system.

The formula for the solid angle $\phi$ conventionally used for vector calculation is:

$$\cos \phi = \frac{x_1 x_2 + y_1 y_2 + z_1 z_2}{\sqrt{(x_1^2 + y_1^2 + z_1^2)(x_2^2 + y_2^2 + z_2^2)}} \quad (4)$$

The scaler product is represented by the numerator and the product of the absolute values of the two vectors is the denominator. The length of vector 1 is:

$$\sqrt{x_1^2 + y_1^2 + z_1^2} \quad (5')$$

while the length of vector 2 is $$\sqrt{x_2^2 + y_2^2 + z_2^2} \quad (5'')$$

The maximum vector of the depolarization is, consequently, that point of the vector loop of QRS whose sum of the quadrants of the three projections x, y and z is greatest, i.e.:

$$V_{max(QRS)} = \sqrt{(x_1^2 + y_1^2 + z_1^2)_{max}} \quad (6')$$

The same therefore applies for the maximum vector of the T-loop:

$$V_{max(QRS)} = \sqrt{(x_2^2 + y_2^2 + z_2^2)_{max}} \quad (6'')$$

Apart from the angle $\phi$, interest is also attached to the position of the maximum vectors in space of QRS and T, so that it is necessary to determine the projections of those vectors in the sloping sagittal plane, on the one hand, and in the frontal plane, on the other. It is pointed out that, for historical reasons in electrocardiography, particularly vector cardiography, the space coordinate axes are designated in a mathematically non-standard manner, the x, y and z axes being associated with respect to the human body, the origin being located approximately centrally in the torso. The up and down axis along the body length is the y axis, the negative y axis pointing upwardly toward the head and the positive y axis pointing downwardly. The horizontal axis is the x axis, the positive x axis extending to the right and the negative x axis to the left. The z axis passes transversely through the body from front to rear and that portion extending to the front front the center is the positive z axis, the rearward portion being the negative z axis. This is in accordance with convention. Contrarily, the orthogonal system according to the invention corresponds to the x, y, $z_o$ system shown in FIG. 1 and slopes by 45° to the sagittal.

Figure 4:
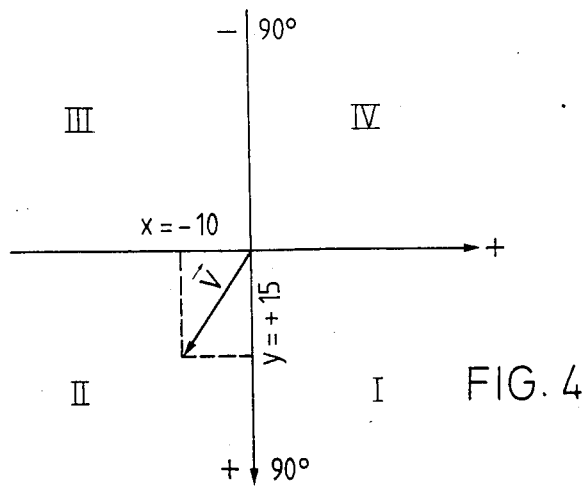
FIG. 4 is a quadrant diagram of the sloping sagittal plane.

The sloping sagittal plane, determined by axes x and y, is subdivided into 360 degrees, the 0° line being horizontally to the rear, the 90° line being to the left and downwardly, 180° to the front, and minus 90° upwardly and to the right, as generally illustrated in FIG. 4. The conversion of the orthogonal coordinates x and y into polar coordinates takes place in accordance with the following formulas, the polar angle in the sloping sagittal plane being designated $\alpha$.

TABLE I

| Quadrant | | |
|---|---|---|
| I | $x+, y+ \quad \alpha = \arctan \frac{y}{x}$ | (7) |
| II | $x-, y+ \quad \alpha = \arctan \frac{y}{-x}$ | (8) |
| III | $x-, y- \quad \alpha = \arctan \frac{-y}{-x}$ | (9) |
| IV | $x+, y- \quad \alpha = \arctan \frac{-y}{x}$ | (10) |

As an example, assume x to have a value of $-10$ and y a value of $+15$. From the polarity, this vector must be in quadrant II. The value of angle alpha is thus arc tan $(15/-10) + 180° = 124°$. This example is illustrated in the second quadrant, FIG. 4.

The same procedure is used when converting the orthogonal coordinates z and y in the frontal plane while using, as a basis, the y axis of the sloping sagittal plane such that 0° is to the lower left and 180° slopes upwardly to the right. The base in the frontal plane is consequently 45° to the body axis, i.e., the sloping sagittal and not the horizontal as in the Frank derivations. The polar angle in the frontal plane is designated beta. Angle beta gives the precise projection of the vector on the frontal plane and, if beta is positive, the vector passes below the sloping sagittal plane. If beta is negative, it passes above the sagittal plane.

The determination of the maximum vectors of QRS, P and T on the basis of the derivations D, A, I and H, A, V, i.e., the use of the electrical derivations signals, is the function of the cardiogoniometer according to the invention. The five derivation signals D (dorsal), A (anterior), I (lower), H (horizontal) and V (vertical) are formed from the four measuring points E1, E2, E3 and E4 (FIG. 1) and in accordance with the above formulas 1, 2 and 3 converted into the three projections x, y and z. The three resulting time-dependent electrical signals form three curved paths corresponding to the projections which are measured at time intervals of, for example, three milliseconds. Finally, these values are stored in a memory for subsequent use. Between the T wave and the following P wave of the next beat, the zero line is determined and corresponding corrections are made. If necessary, all of these stored values are referenced to the established zero value. The maximum sum quadrant of $x_1$, $y_1$, and $z_1$ on the one hand, and $x_2$, $y_2$, and $z_2$ on the other is determined. On the basis of this data, the cardiogoniometer then calculates the value of cos $\phi$ according to formula 4 and determines therefrom arc cos $\phi$.

Thus, almost immediately, the angle $\phi$ of a single given heartbeat is made available. The cardiogoniometer then calculates the angles $\alpha$R, $\alpha$T, $\beta$R and $\beta$T on the basis of formulas 7–10 and this data, including the base data $x_1, y_1, z_1, x_2, y_2, z_2$ are stored. Thus, in all, 11 parameters can be provided for the same heartbeat while the beat interval is available as a 12th parameter. Alternatively, the problem of the slowly varying zero line can be solved with a digital or analog high-pass filter.

Figures 5, 6:
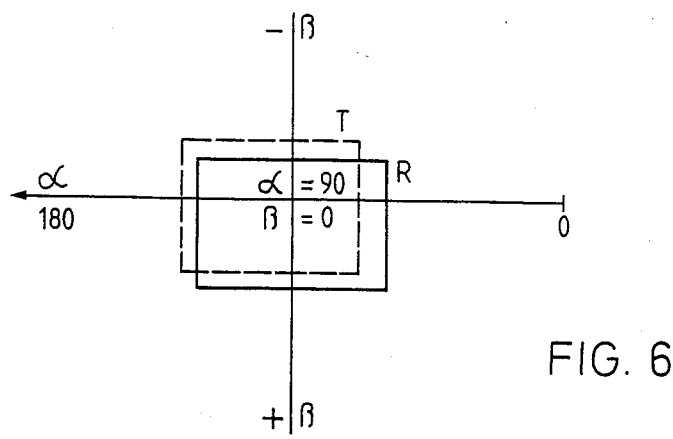
FIG. 5 is a tabular presentation of heart parameters in accordance with the invention.
FIG. 6 is a diagram showing the establishment of a statistical normal range for T and R vector directions in cartesian coordinates.
Figure 6:
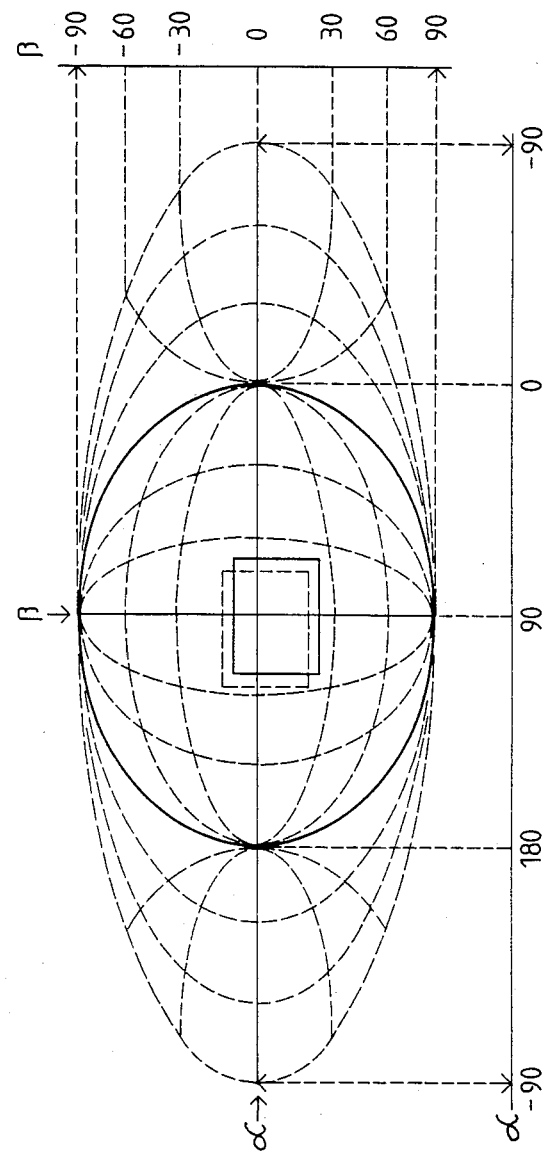
Figure 9:
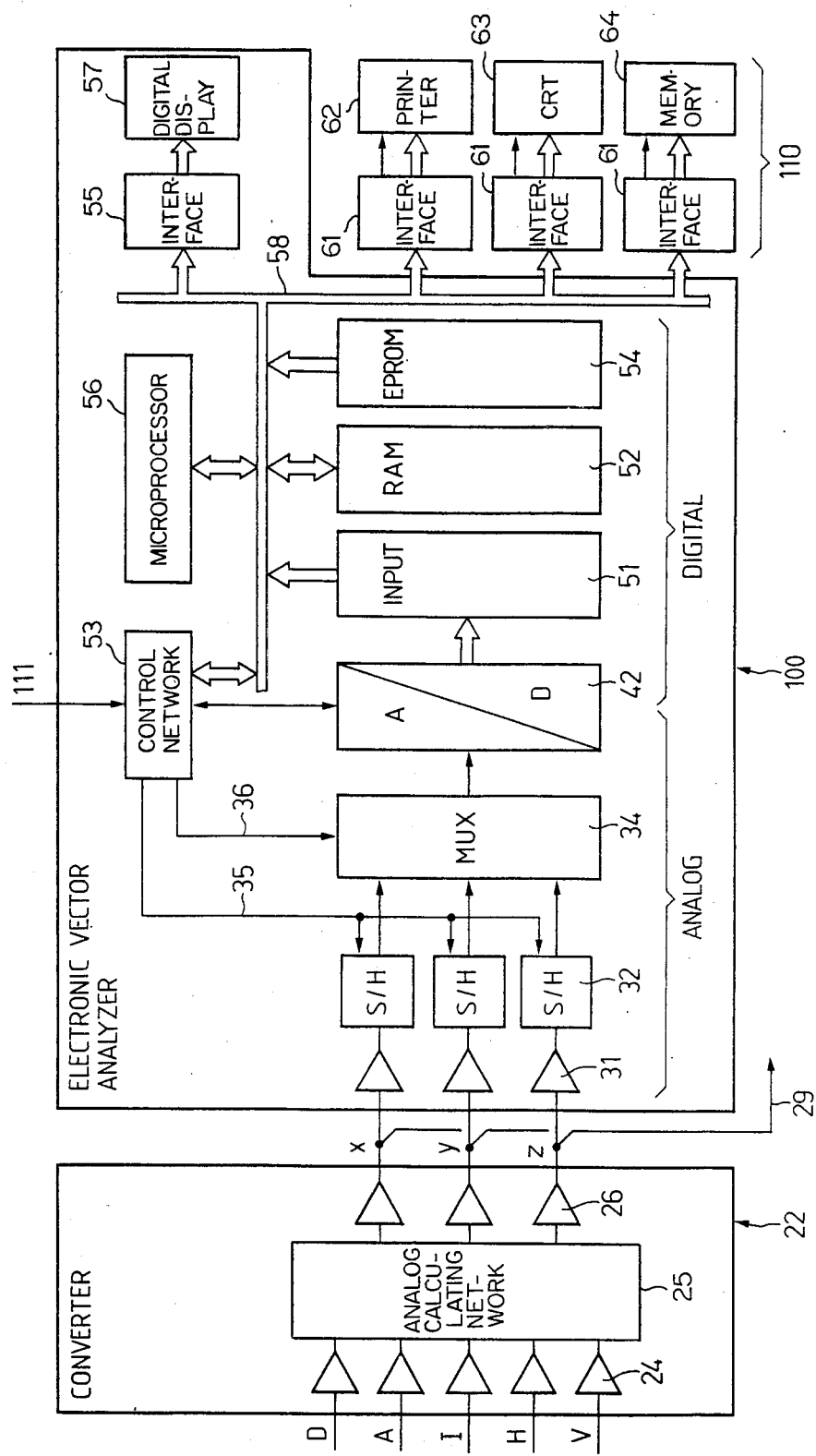
FIG. 9 is a schematic diagram in block form, of an embodiment of a cardiogoniometer in accordance with the invention.

For the purpose of checking the cardiogoniometer in operation it is possible, for example, to simultaneously jointly record projections x, y and z on a three-channel electrocardiograph as illustrated in FIG. 9. The signals complex calculated by the cardiogoniometer are marked on the strips containing the curve traces. As a result, a reading is obtained which corresponds or is similar to the conventional representation of the ECG while there is also a graphic representation of certain calculated data or actual projections of the derivations. According to a practical embodiment of the cardiogoniometer, six measured quantities $\phi$, $\alpha R$, $\beta R$, $\alpha T$, $\beta T$, as well as the beat interval, are continuously printed on a printer (FIG. 5). In this way, measurement takes place roughly every third heartbeat. Thus, in a short time, a series of measurements can be performed on patients, making it possible to determine statistical values such as the mean value and standard deviation.

As an example, the standard values are determined on a group of 100 test subjects with healthy hearts and fulfilling the following criteria:

1. No clinical criteria indicating an organic heart disease;
2. Normal ECG in the 12 standard derivations according to the prior art;
3. Constant values for all five parameters $\phi$, $\alpha R$, $\alpha T$, $\beta T$ according to the invention over an interval of 10 heartbeats, the dispersion being less than plus or minus five degrees, which means that for each heartbeat the depolarization and repolarizations take the same "electrical path".

The thus determined values read as follows:

TABLE II

|   | $\phi$ | $\alpha R$ | $\beta R$ | $\alpha T$ | $\beta T$ |
|---|---|---|---|---|---|
| ± | 15° | 89.9° | 9.4° | 98° | 3.2° |
| s | 7.9° | 11.6° | 7.8° | 10.5° | 8.8° |

When choosing ±2 standard deviations as the standard limits, the following standard values (rounded off) are obtained for subjects with healthy hearts in the supine position:

$\phi = 0°$ to 31°

$\alpha R = 65°$ to 115°

$\beta R = +25°$ to $-10°$ $\alpha T = 75°$ to 120°

$\beta T = +20°$ to $-15°$

This group contained 56 men and 44 women, the age of the test subjects ranging between 14 and 89 years, 95.4% of the cases being statistically covered by plus or minus two standard deviations.

In the normal case, the maximum vectors for depolarization and repolarization are very close together, the true angle in space $\phi$ representing 0° to 31° (15°±16°). With an angle smaller than 31°, pathological conditions can still exist if both the depolarization and repolarization are disturbed. Thus, great importance is attached to the location of $R_{max}$ and $T_{max}$ with respect to the sagittal and frontal planes. These are located in a small circle around the central axillary line (angle alpha=90°) and slightly above or below the sloping sagittal plane (angle beta=0°). FIG. 6 graphically illustrates these points.

A divergence of the vectors from this electrical center (according to FIG. 6' and indicated by a longer vector arrow) to the front, rear, top and bottom and, finally also on the rear surface (referring to the representation on the spherical surface according to FIG. 6') means a pathological finding. Thus, there are typical displacements of the R-vector, e.g., in the case of bundle-branch blocks LBB and/or RBB and other blocks, as well as in the case of R-losses after infarctions. Moreover, each repolarization disturbance is manifested by a divergence of the T-vector in the opposite direction from the focus of the lesion.

In the left side position, the heart is generally rearwardly displaced by approximately 10°. Thus, with respect to the angle alpha, the standard values are displaced 10° rearwardly to: $\alpha R = 55°$ to 105°; $\alpha T = 65°$ to 110°.

The hitherto widely-held idea that, in the left position, perfusion problems to the right coronary artery (RCA) could occur was confirmed when using the invention in comparison with coronarograms of coronary patients, so that in the left side position in the case of ischemia in the region of the right coronary artery, there is a forward displacement of the T-vector (alpha T becomes larger than 110°). There is also an opening for increase in the angle $\phi$ which designates the true angle in the space between the maximum vectors QRS and T. Thus, as a routine measure, a cardiogoniogram in the left position should always be taken as a small functional test of the RCA.

A more or less pronounced fluctuation of the T-vector values was found in series measurements on patients with coronary insufficiencies in the presence of technically perfect projections x, y and z. The standard deviation of 10 measurements is consequently above the arbitrarily fixed value of 5°, probably indicating myocardial ischemia. The cardiogoniometer and derivation process according to the invention made it possible, for the first time, to observe this phenomenon of floating in a patient in status anginosus shortly before the occurrence of a front wall infarction.

Figure 7A:
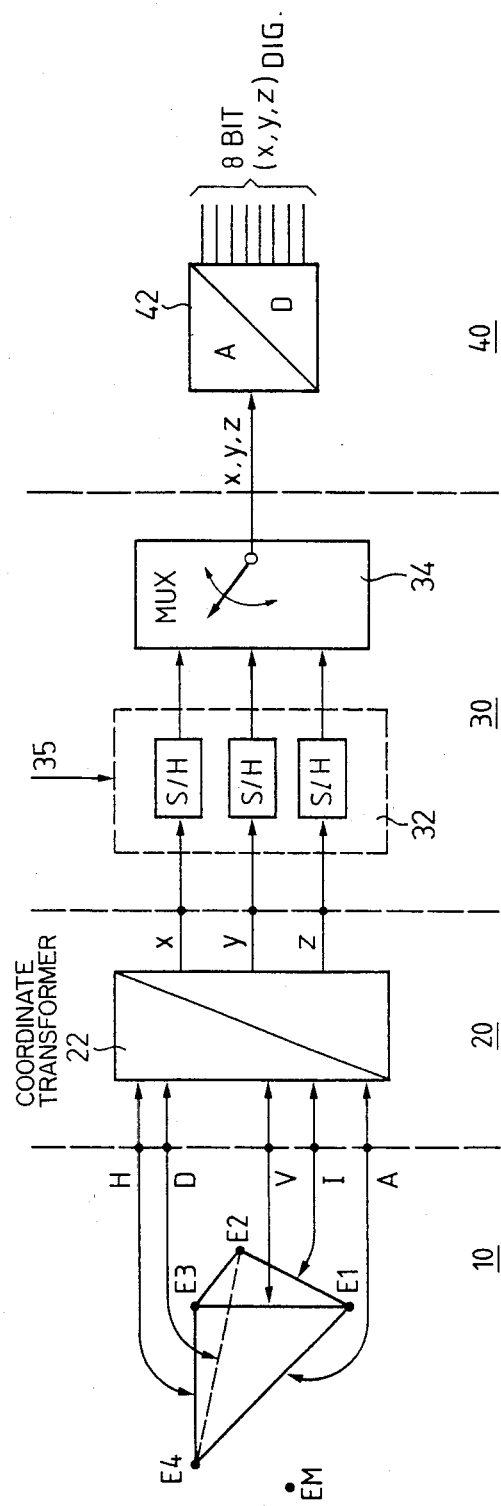
FIGS. 7A and 7B, taken together, are a schematic diagram, in block form, of an apparatus in accordance with the invention.
Figure 7B:
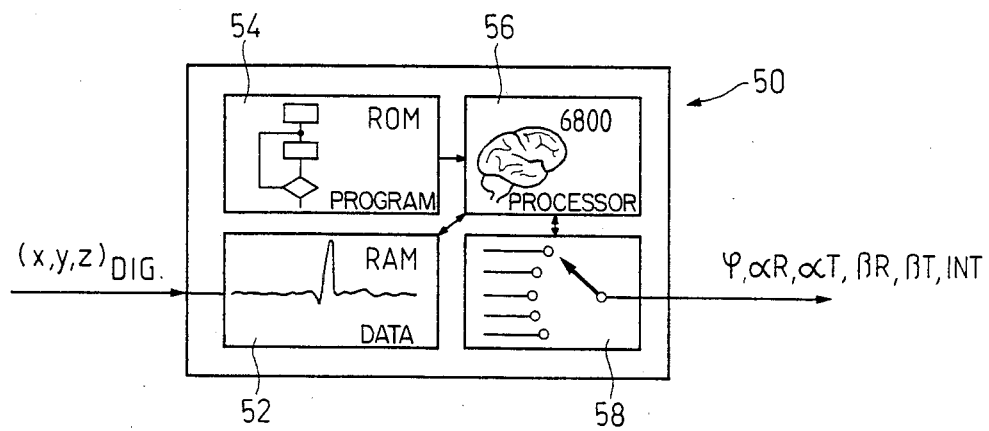

FIGS. 7A and 7B show in simplified form the apparatus for performing the process. In FIG. 7A, information obtained from the human body is processed in four subsequent apparatus stages 10, 20, 30 and 40 up to digitalization. The first stage 10 includes circuit means for obtaining signals from the body and shows the derivations as represented generally in FIG. 1. These derivations are obtained by the derivation process according to the invention with the aid of four thorax electrodes E1–E4 and a ground electrode EM which is preferably fixed to the right arm. Of the six derivations which can, in principle, be obtained from this tetrahedron, three are linearly independent and, in the present example, five are used. The derivation not further identified between points E2 and E3 is not used because it is considered to belong to the uninteresting projection plane or is omitted as a redundant pair. The five derivations used are designated H for horizontal, D for dorsal, V for vertical, I for lower, and A for anterior.

The electrical signals of these five derivations are fed by derivation stage 10 into the coordinate transformation stage 20 wherein the desired projections are carried out in an orthogonal system. This is performed by a network 22, which is preferably an analog network, although it is also possible to directly process three linearly independent derivations in a digitizing coordinated transformation stage 20. The projections x, y and z pass from the coordinate transformation stage 20 into a sampling stage 30 where they are sampled by sample and hold circuits 32. A multiplexing circuit 34 converts the information from parallel into series and also forms part of the sampling stage 30.

The serially arranged data representing the individual projections now passes from sampling stage 30 into a digitizing stage 40 which, in a simplified representation, comprises an analog-to-digital converter 42. The x, y, z projections are, for example, digitized as eight bit words in this stage, this arrangement having proved adequate for practical purposes. However, for more detailed resolution of the measurements or for discovering still unknown effects within the electrical signals, it is clearly possible to provide a 16-bit or larger word arrangement. Symbolically, the digitized projections are designated $(x, y, z)_{dig}$.

FIG. 7B shows in highly simplified form the main part 50 of the cardiogoniometer in accordance with the invention, wherein the digitized projections $(x, y, z)_{dig}$ are converted into the corresponding informative quantities. In accordance with the previously described example, these are the angles $\phi$, wherein $\phi$ is the true angle in space between the QRS and T maximum vectors, together with the values $\alpha R$, $\alpha T$, $\beta R$ and $\beta T$ related to the coordinate system. The heartbeat interval is derived, for example, between two QRS flanks. The cardiogoniometer part 50 as shown includes a memory 52 containing the actual heartbeat data, this memory or store being of a random access type; a memory 54 containing the processing program; and a microprocessor 56 which can be, for example, a Motorola Type 6800, and which is used for this data management and also is used in the present cardiogoniometer for control of the various functions; as well as the symbolically represented switching network 58, for example, a bus system for making available interesting data from a memory, e.g., memory 64 (FIG. 9), which can naturally also be supplied in serial manner from the cardiogoniometer. Strictly speaking, the data is only obtained after conversion in peripheral devices such as, for example, a display unit, a printer, a screen or the like, but this simplified description is only intended to show how the electrodes attached to the patient lead to very exact diagnostic results by signal and data processing.

Figure 8:
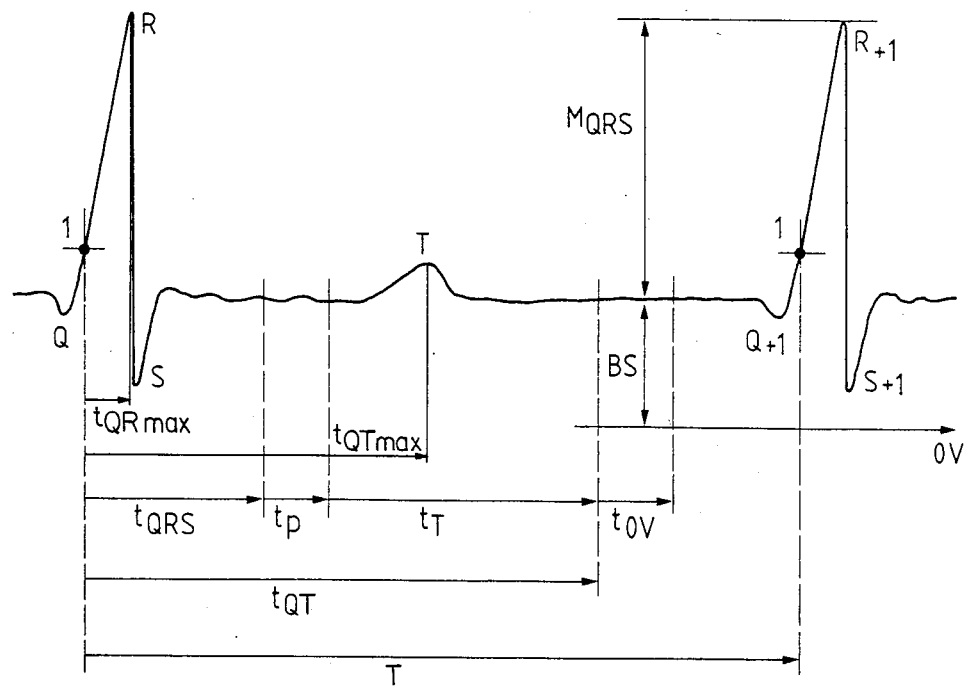
FIG. 8 is a segment of a typical electrocardiogram wave form.

FIG. 8 shows the various stages for processing of a heartbeat cycle interval as a function of time. The typical picture of an ECG curve is shown in partial form in the period from a completely acquired QRS-complex wave to a completely acquired $QRS_{+1}$ complex wave. The steep QR-flank is particularly suitable for triggering functional sequences. Following QR triggering at a threshold value 1, a start is made to the measurement of the beat interval $\tau$ as well as the subdivision of $\tau=(QRS+1-QRS)$ into various data windows $t_{QRS}$; $t_P$; $t_T$; $t_{OV}$; $t_{QT}$; i.e., into intervals which are to be individually stored, vital importance being attached to the time $t_{OV}$. At this point, the base line of the curve is measured then averaged and compared with the electrical neutral point at zero volts (OV). This base line voltage BS is used as a correction value for all of the amplitude dependent quantities such as, for example, the indicated QRS magnitude $M_{QRS}$ and represents the actual biological zero line.

FIG. 9 shows in somewhat more detail the cardiogoniometer according to the invention. The electrical measuring values of the five derivations D, A, I, V, and H pass through individual input amplifiers 24 to an analog calculating network 25 which represents the essential part of the coordinate transformation circuit 22 in which is determined the projections x, y and z according to the given formulas and the signals of the projection quantities are made available. These signals are subsequently amplified in output amplifiers 26 to enable them to be recorded in a parallel-operating cardiograph or its recording instrument and, for this purpose connecting lines 29 are provided.

The x, y, z signals are supplied through individual amplifiers 31 to sample and hold circuits 32 the sample times of which are determined by signals provided from a control program on line 35 from control circuit 53. In synchronism therewith a multiplexer 34 is controlled for sampling the signals which are provided and this is under the control of the same control network 53 through line 36. This circuit portion incorporates the analog signal processing, the analog signals being converted to digital data in analog-to-digital converter 42. As previously indicated, in the present embodiment an 8-bit format is used, but this can be expanded without significant additional expenditure to a 16-bit format. The digital data processing includes an input circuit 51, a data store 52, shown as a random access memory, and a control program store 54, shown as an EPROM, as well as an associated microprocessor 56. The random access store is used for data storage while the EPROM is preferred for storing the control program. To have control of the calculated value done by the microprocessor, a digital display 57 interfaced by interface network 55 is used. For more flexibility as to peripheral equipment the bus 58 ca be used with, as options, a printer 62, a CRT-display 63, mass memory means 64 like tapes, floppy-drives etc. all interfaced by corresponding interface networks 61. All these blackboxes are subsumized under a peripheral evaluation block 110. As shown in FIG. 7B, the stored data relate to the digitized heart rhythm curves according to FIG. 8 while the control program is represented in the structogram of the process illustrated in FIG. 11.

Figure 10:
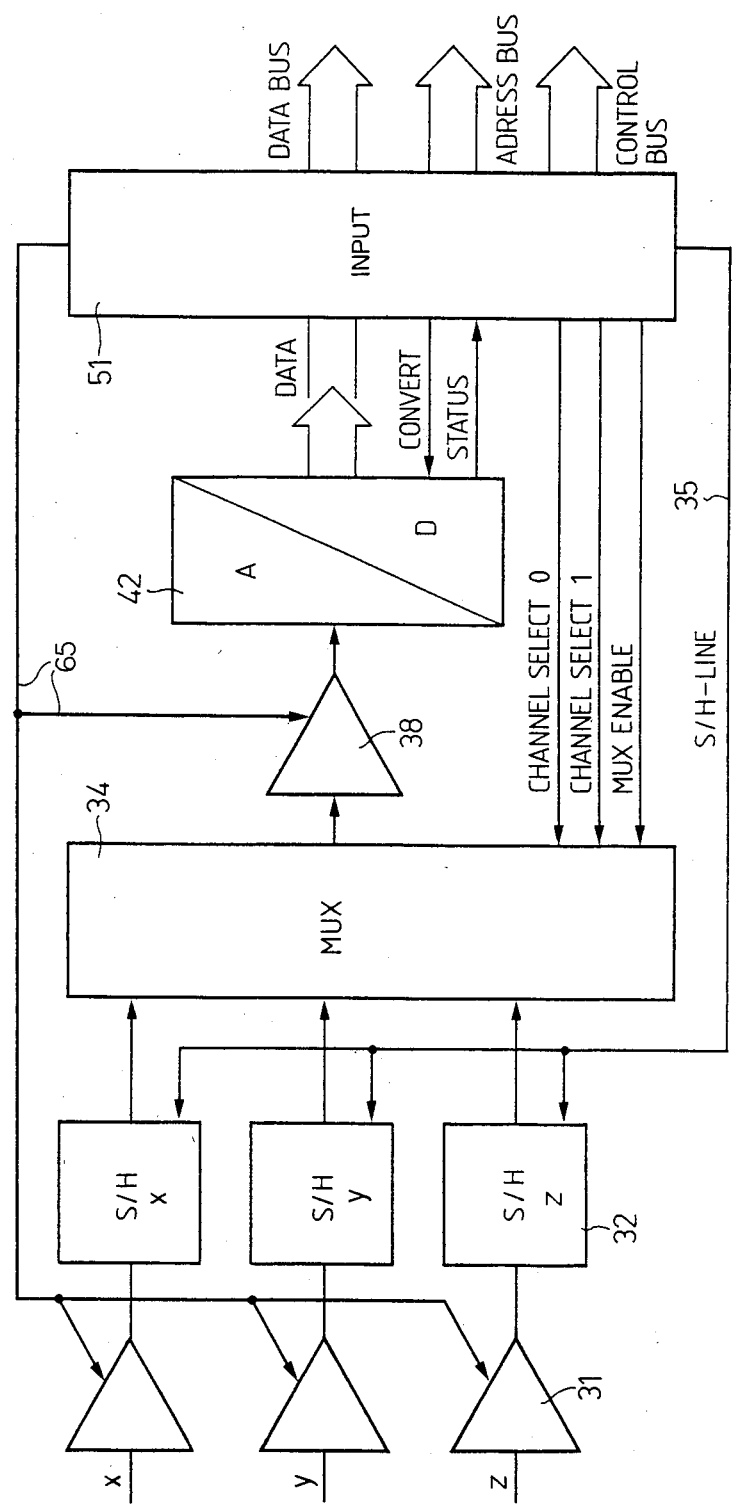
FIG. 10 is a schematic diagram, in block form, of a portion of the vector analyzer of the apparatus of FIG. 9.

A detailed description of the analog-to-digital adapter module will be given before the structogram is described. The network in question is shown in FIG. 10 and includes the x, y and z input amplifiers 31, the outputs of which are connected to the associated sample and hold circuits 32. As previously indicated, the sample and hold circuits are synchronized from input circuit 51 to the microprocessor by the control network 53 and control line 35. Apart from the x, y and z data signals, which are at the input end in analog form, the multiplexer, receives channel selection instructions 0 and 1 as well as a multiplexer release instruction from digital input circuit 51. Furthermore, input amplifiers 31 and an intermediate amplifier 38 are controlled from the same circuit as to the level of amplification, by means of corresponding signals transmitted through line 65. The heart signals from multiplexer 34 which are to be digitized are intermediately amplified in amplifier 38 and delivered to the ADC 42. This converter is additionally connected through a separate line for status indication purposes to input circuit 51 in addition to the data bus. The input circuit 51 starts the ADC conversion by means of a "convert" signal on a separate line. In the conventional manner, the input circuit 51 is connected to the microcomputer by means of three bus systems, the data bus, the address bus, and the control bus.

Figure 11:
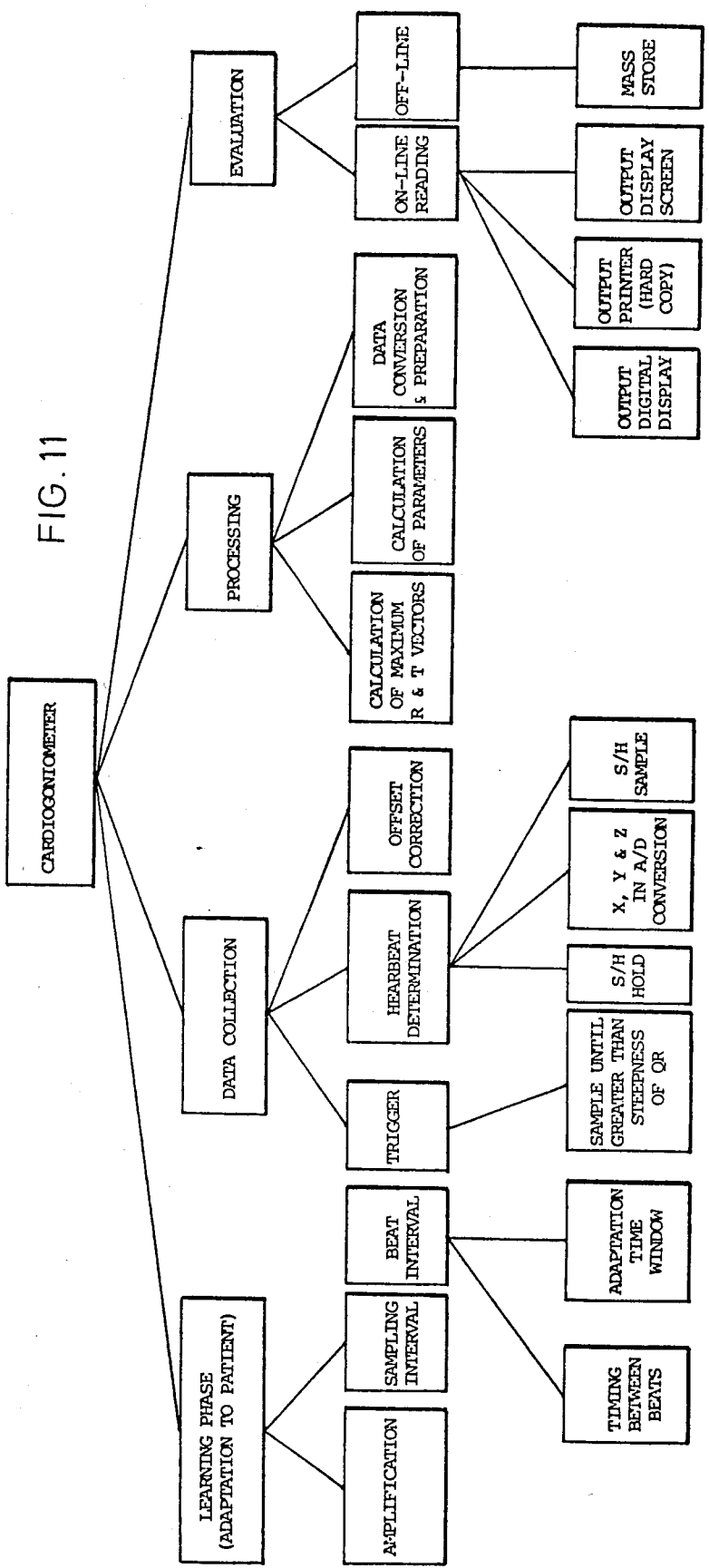
FIG. 11 is a diagram illustrating the method in accordance with the invention.

Finally, FIG. 11 shows a Jackson Structogram in simplified form. Jackson Structograms are read from top to bottom and from left to right. Examining this structogram from the left in the drawing, there is in a first stage a learning phase which represents the adaptation of the equipment to the patient and the establishment of parameters for the amplification, sampling intervals and beat intervals result from this phase. For this purpose, three to six cycles of the type shown in FIG. 8 are used. From the beat intervals, the time measurement between two heartbeats is obtained, as well as the patient-specific adaptation of the various data windows shown in FIG. 8. This followed by data acquisition from which are obtained trigger points, the heartbeat intervals, and the offset correction. The heartbeat signals are continuously sampled, for example, in three millisecond intervals. The values of a heartbeat cycle are stored and evaluated only after the trigger point has been detected. This trigger point is determined by exceeding a predetermined steepness of the QR flank. Trigger point searches and heartbeat interval determinations are accomplished on a repetitive basis. Every third heartbeat can easily be determined at the data conversion rate of the present embodiment. Every heartbeat can be determined if the necessary additional expenditure for faster circuitry is made.

In the preliminary development stage, the processing of these signals relates to the calculation of the maximum vectors R and T, the calculation of the quantities $\alpha R$, $\alpha T$, $\beta R$, $\beta T$, etc. as well as the data conversion and preparation. The calculated quantities are then used for evaluation purposes in so-called "on-line" readings, i.e., readings of measured values are presented on a real-time basis for diagnosis during the measurement on the patient, often called the bedside method. These include the measuring data readout on a digital display, the readout thereof and of further data on a printer for recording and filing purposes, as well as the readout on a screen in the form of a graph. Then, in so-called "off-line" evaluations, i.e., away from the patient, stored signals from memory 52 are made ready for further data processing, such as statistical evaluation and the like which, transferred to large data files, can be further evaluated with somewhat more complicated programs in larger computers.

It is not possible with prior art electrocardiography to completely determine the electrical processes of the heart because such devices only involve measurements in one plane. Such analysis is only possible with a three-dimensional derivation system, i.e., vector cardiography. Cardiogoniometry, as a first stage of bedside vector cardiography, now uses a novel and technically simple three-dimensional derivation system which permits the three-dimensional determination of the electrical processes at the patient's side. Initially, it only determines the maximum vectors of the QRS loop and the T loop. The information content of these two quantities is still very large.

It was not previously possible to obtain more complex evaluations of measured values at the bedside. It was conventional practice, for example as described in U.S. Pat. No. 4,106,495, Kennedy, to collect measured data on the body and record these, followed by their time-consuming evaluation on a computer. It was not unusual for the patient to be dead before his data underwent evaluation. Thus, the virtually direct determination, evaluation and representation of complex relationships within one or a few heartbeats meets a practical need. On-line evaluation makes it possible to observe the reaction of the heart, for example, on a screen, in the case of medical use on the ergometer and with manipulation of all types.

The QRS vector corresponds to the so-called electrical heart axis. Its position in space is now qualitatively characterized by the terms transverse or lateral position, steep position, horizontal position, left type, etc. In place of these qualitative terms, cardiogoniometry (KGM) provides a direction which is clearly defined in space. Even minor changes to this direction can be established in the course of time, e.g., increases or decreases of heat dilatation or hypertrophy, the development of a left anterior fascicular block, and the like, before it is possible to note any change in the standard electrocardiogram such as when measuring according to the prior art. Changes to the QRS vector in the acute test, such as, for example, the position change of the QRS vector in the left side position, or after stressing or administering medications such as, for example, nitroglycerine, make it possible to detect local and small circulation problems in the septal branches of the coronary arteries.

Position changes of the T vector give information on the heart repolarization conditions, i.e., on disturbances of the metabolism or perfusion problems in the myocardium. If there is an ischemia of the rear wall (RCA) the T vector is no longer in the standard region and is, instead, positioned further forward. In the case of an ischemia of the front wall (LCA) it is outside the standard range and further to the rear. These changes also appear in the case of local metabolism problems of the front or rear wall. If the myocardium at rest is still sufficiently perfused, then the T-vector will probably still have normal values. In this case a relative ischemia, that is a latent coronary insufficiency may be demonstrated by decreasing the coronary throughput, e.g. by means of nitroglycerine. Nitroglycerine decreases preload as well as the systolic volume. This results in a lower level of blood pressure. But nitroglycerine also increases the frequency of the heart beat. Both effects tend to reduce the flow through the coronaries which is especially true for slightly contracted ones. As a result of those effects, the T-vector departs from the ischemic myocard position. This effect is sufficiently distinct so that exercising may not be necessary.

The T-vector may drift in a rather limited area if the coronary-stenosis is not total or not complete. The earlier mentioned effect called floating can be found by cardiogoniometric measurements on a series of heart cycles. This effect may be demonstrated e.g. after short heart stops.

Cardiogoniometry may prove very useful for supervision of patients suffering from heart diseases especially after myocardiac infarctus or patients submitted to heart surgery, because both vectors react very sensitively to disturbances of the circulation with the heart.

As cardiogoniometry is a non-invasive method lacking of unwanted side-effects it is well adapted to be used for periodic tests of the heart functions and to early detect latent coronary insufficiencies in patients liable to suffer from myocardial infarctions such as, for example, smokers, diabetics, managers and hypercholesterolemics. As the method acts very sensitively and directly to perfusion problems of the coronary arteries, it should also be suitable for checking heart-active medications.

As the cardiogoniometer does not merely store the maximum vectors, but, rather, stores both vector loops in toto, it is possible to obtain further quantities or magnitudes in off-line processes. Examples are random intervals such as $tQR_{max}$ and QR, or $tQT_{max}$ and QT, as well as the representation of a vector X at time X, e.g., initial vectors. It is then possible to display these on a screen which applies not only to the maximum vectors but also to the entire QRS and T loops, either individually or in series for showing, for example, a possible floating effect. Thus, an accurate and completely computerized heart diagnosis results and, as a result of the very small size of the cariogoniometer in accordance with the invention, it is particularly suitable for use in outpatient departments.

While certain advantageous embodiments have been chosen to illustrate the invention it will be understood by those skilled in the art that various changes and modifications can be made therein without departing from the scope of the invention as defined in the appended claims.

What is claimed is:

1. A method for detecting electrical, heart-related signals in the natural bioelectrical field of a human body comprising the steps of:
   providing apparatus for recording and analyzing electrical signals, providing a plurality of electrodes, electrically connecting said electrodes to said recording and analyzing apparatus;
   positioning a first one of the electrodes at point V4 according to Wilson;
   positioning a second one of the electrodes at point V8 according to Wilson;
   positioning a third one of the electrodes generally vertically upwardly with respect to the body above the first electrode with respect to the upright body at a distance equal to the distance between the first and second electrodes multiplied by a factor having a value between 0.6 and 0.8;
   positioning a fourth one of the electrodes along a line generally perpendicular to the line between the first and third electrodes and toward the right body side therefrom at a distance equal to the distance between the first and second electrodes multiplied by a factor having a value between about 0.6 and 0.8 such that the first, the second and the fourth electrode together define a plane (x,y) of a system of orthogonal axes (x,y and z), and said plane corresponding in a statistical range to a plane defined by a spatial vector-loop of the healthy heart; and
   computing the electrical signals produced by the electrodes to determine parameters of projections of a spatial vector representing the electrical field of the heart on at least one of the planes defined by the axes of said system.

2. A method according to claim 1 wherein the distance between the first and third electrodes and the distance between the third and fourth electrodes are both equal to the distance between the first and second electrodes multiplied by $1/\sqrt{2}$.

3. A method for representing the electrical field generated by the heart as a spatial vector defined by coordinates in a system of orthogonal axes whereby the electrical field produces electrical signals in a plurality of electrodes on a human body, comprising the steps of:
   positioning a first electrode at point V4 according to Wilson,
   positioning a second electrode at point V8 according to Wilson,
   positioning a third electrode substantially vertically above the first electrode with respect to the upright body at a distance equal to the distance between the first and second electrode multiplied by a factor having a value between 0.6 and 0.8,
   positioning a forth electrode along a line substantially perpendicular to the line between the first and third electrode and toward the right body side therefrom at a distance equal to the distance between the first and second electrodes multiplied by a factor having a value between about 0.6 and 0.8 such that the first, second and fourth electrode together define a plane of location of the axes of said system of orthogonal axes, said plane substantially corresponding to a plane defined by a spatial vector-loop of the healthy heart, and
   computing the electrical signals produced at the electrodes in order to get parameters of projections of said spatial vector on at least one of the planes of said system of orthogonal axes.

4. A method for representing the electrical field generated by the heart of a subject as a spatial vector defined by coordinates in a system of orthogonal axes whereby the electrical field produces electrical signals in a plurality of electrodes on the subject, comprising the steps of:
   positioning three electrodes on the subject, said electrodes forming a plane containing an area defined by the projection of the spatial vector while the spatial vector is executing a heart cycle and whereby this area is maximum, and
   positioning another electrode outside of said plane and computing values of said spatial vector out of electrical signals produced at the electrodes, said values of said spatial vector corresponding to projections of said spatial vector in at least one of the planes defined by the locations of said electrodes.

5. A method according to claim 1 or claim 4, and the steps of: determining maximum values of the spatial vector, determining timing relations of such maximum values with respect to the beginning of the QRS-wave of the heart cycle, and determining the angle between two of said maximum values of the spatial vector.

6. A method according to claim 1 or claim 4, and the steps of: determining the maximum values of the spatial vector, determining timing relations of such maximum values with respect to the beginning of the QRS-wave of the heart cycle, determining both said maximum values and said timing relations for the QRS-, P- and T-wave of the same heart cycle and computing reference values of the maximum vector according to the principles of statistics.

7. A method according to claim 1 or claim 4, and the steps of: determining the maximum values of the spatial vector, determining timing relations of such maximum values with respect to the beginning of the QRS-wave of the heart cycle, determining both said maximum values and said timing relations for the QRS-, P-, and T-wave of the same heart cycle, and computing mean values and standard deviation values.

8. A method according to claim 1 or claim 4, and the steps of: determining the maximum values of the spatial vector, determining timing relations of such maximum values with respect to the beginning of the QRS-wave of the heart cycle, determining both said maximum values and said timing relations for the QRS-, P-, and T-wave of the same hearty cycle, and establishing a range for normal values of the maximum vectors in healthy subjects.

9. A method according to claim 1 or claim 4, wherein said subject is a mammal.

10. A method according to claim 1 or claim 4, wherein said subject is a human being.

11. A method for representing the electrical field generated by the heart as a spatial vector defined by coordinates in a system of orthogonal axes wherein the electrical field produces electrical signals in a plurality of electrodes on a human body containing said heart, comprising the steps of:

positioning a first electrode at point V4 according to Wilson, positioning a second electrode at point V8 according to Wilson, positioning a third electrode substantially vertically above the first electrode with respect to the upright body at a distance equal to the distance between the first and second electrode multiplied by a factor having a value between 0.6 and 0.8, positioning a fourth electrode along a line substantially perpendicular to the line between the first and third electrode and toward the right body side therefrom at a distance equal to the distance between the first and second electrodes multiplied by a factor having a value between about 0.6 and 0.8, computing differences of the values of the electrical signal measured between each pair of said electrodes, computing a projection of the spatial vector of the electric activity of the heart on planes of a system of axes defined by the locations of the electrodes out of said differences of said values, and transforming said computed projections of the spatial vector into projections of the spatial vector within the system of orthogonal axes, said orthogonal axes defining a plane corresponding to a plane defined by the first, the second and the fourth electrode.

12. A method according to any one of claims 1–11, and the step of representing the spatial vector during QRS-portions of the heart cycle.

13. A method according to any one of claims 1–11, and the step of representing the spatial vector during T-portions of the heart cycle.

14. A method according to any one of claims 1–11, and the step of representing the spatial vector during P-portions of the heart cycle.

15. A method according to any one of claims 1–11, and the step of measuring the duration of QRS-, T- and P-portions of the heart cycle.

16. A method according to any one of claim 1–11, and the steps of: determining maximum values of the spatial vector, determining timing relations of such maximum values with respect to the beginning of the QRS-wave of the heart cycle, determining both for the QRS-, P- and T-wave of the same heart cycle.

* * * * *